United States Patent [19]

Lustig et al.

[11] Patent Number: 4,728,292

[45] Date of Patent: Mar. 1, 1988

[54] DENTAL APPARATUS

[75] Inventors: Leopold P. Lustig, Newton, Mass.; Peter Malata, Salzburg, Austria; Walter Kracht, Lemgo, Fed. Rep. of Germany

[73] Assignee: Gebr. Brasseler, Postach, Fed. Rep. of Germany

[21] Appl. No.: 810,984

[22] Filed: Dec. 19, 1985

[51] Int. Cl.[4] .............................................. A61C 5/04
[52] U.S. Cl. .................................... 433/225; 433/128; 433/167
[58] Field of Search ............... 433/225, 128, 127, 147, 433/167

[56] References Cited

U.S. PATENT DOCUMENTS

| | | | |
|---|---|---|---|
| 1,837,403 | 12/1931 | Brown | 433/128 |
| 2,029,734 | 2/1936 | Meitzler | 433/80 |
| 2,338,437 | 1/1944 | Karlstrom | 433/128 |
| 2,701,914 | 2/1955 | Dietrich | 433/128 |
| 2,801,111 | 7/1957 | Kaltenbach | 433/128 |
| 2,994,129 | 8/1961 | Tanner et al. | 433/127 |
| 4,219,620 | 8/1980 | Carse | 433/225 |

FOREIGN PATENT DOCUMENTS

| | | | |
|---|---|---|---|
| 0145652 | 6/1985 | European Pat. Off. | 433/225 |
| 8301895 | 6/1983 | PCT Int'l Appl. | 433/225 |

Primary Examiner—John J. Wilson
Attorney, Agent, or Firm—Wolf, Greenfield & Sacks

[57] ABSTRACT

A dentinal retention pin and dental tool for inserting the retention pin into the healthy dentine portion of a tooth. A cylindrical hole with a beveled top is predrilled in the tooth to receive a threaded end portion of the pin such that the threads cut into the dentine to secure the pin. A chamfered stop is positioned above the threaded portion, which seats against the beveled top of the hole to limit penetration of the pin into the tooth. The pin is dimensioned to stop before the threaded portion engages the bottom of the hole. A supra-coronal portion of the pin pertrudes above the stop and provides a surface for securely attaching a reconstructed coronal portion to the tooth. A manipulating section of the pin attaches to the supra-coronal section by a frangible link. The manipulating section comprises a cylindrical extension of the pin having a flat engagement surface in a plane approximately along the diameter of the pin. The dental tool for operating the pin has a socket for receiving and retaining the manipulating section, the socket having a flat surface for engaging the corresponding flat engagement surface of the pin. The pin is elastically retained in the socket to permit self-alignment of the pin along the axis of the hole within a range of tool positions.

14 Claims, 13 Drawing Figures

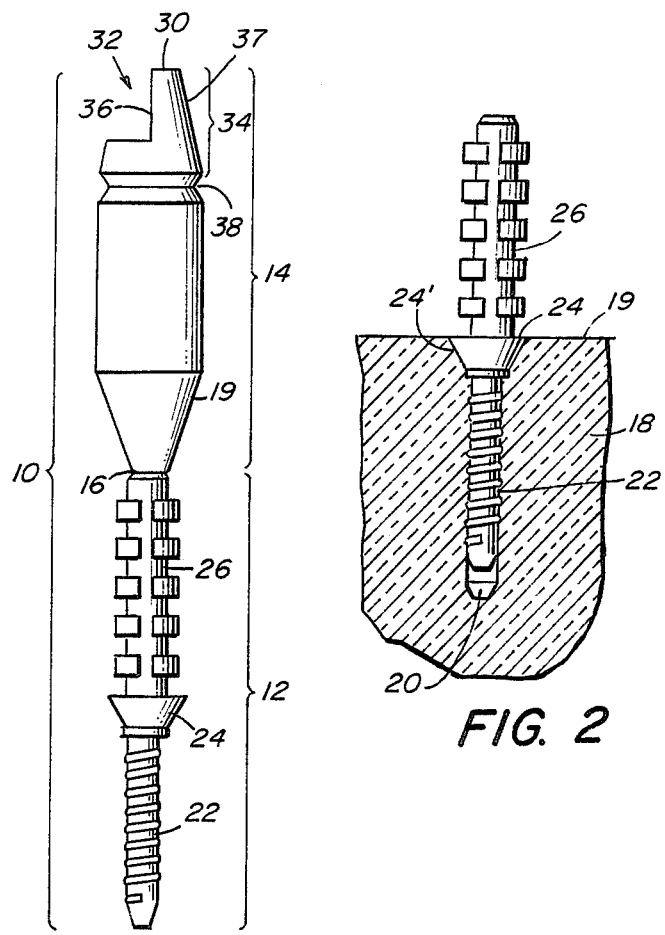
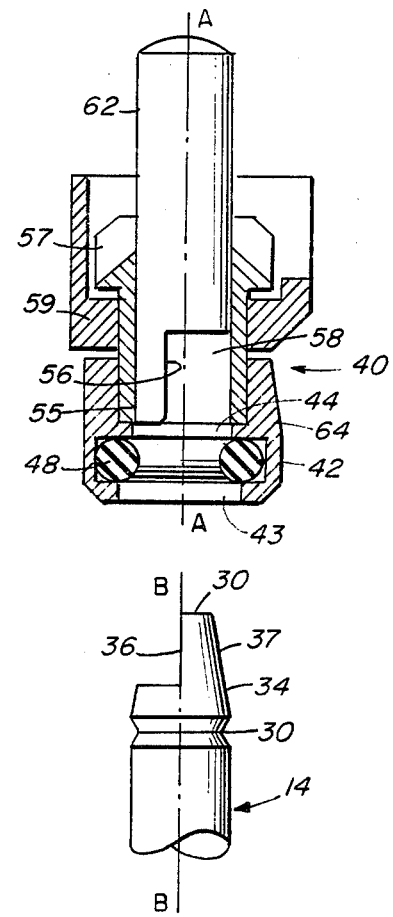
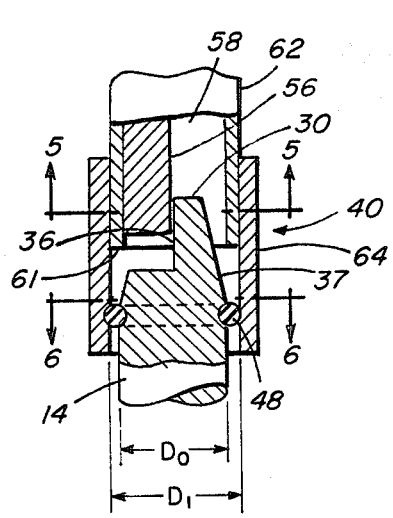
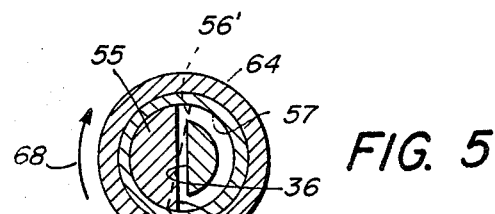
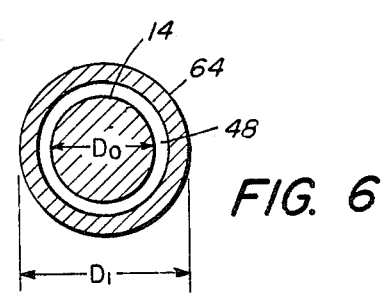

DENTAL APPARATUS

BACKGROUND OF THE INVENTION

The present invention relates to a dentinal retention or anchoring pin for mechanically securing to the healthy dentine or root portion of a tooth a restoration of the coronal portion. The invention provides a novel tool and manipulator for inserting the pin into the dentinal portion of the tooth, together with novel storage and delivery systems.

The dental practitioner is frequently confronted with the need to replace the top or coronal portion of a tooth which may have been fractured or otherwise lost due to trauma or disease. Numerous designs of dental anchors are known which fit into predrilled channels in the tooth understructure and protrude supra-gingivally to provide an anchor or mechanical link for attaching a restoration to the dentinal portion. Such dental anchors must be very precisely inserted to avoid damaging the dentine, and especially to avoid misalignment with the channel, either of which can lead to tooth fracture. Further, due to the space limitations generally restricting dental work in the patient's mouth, an effective but compact connection between the anchor and the inserting tool is desirable, but up to now such a compact connection has not been available.

SUMMARY OF THE INVENTION

Accordingly, it is an object of the present invention to provide improved methods and means for securing a coronal restoration of a tooth to the healthy dentinal understructure.

Another object of the invention is to provide a pin and pin-holder for inserting the pin in a predrilled hole in the dentinal portion, which in use is self-aligning along the axis of the predrilled hole within a range of manipulating tool positions.

Another object is to provide a storage and delivery system which will enable a pin-holder and manipulator to pick up a pin without the need to handle the pin.

These and other objectives are achieved in accordance with the present invention, wherein a dentinal retention pin structure is constructed having four functionally distinct component parts, or portions:

A first portion of the pin structure is threaded to securely engage in a predrilled channel within the tooth dentine. The threaded engagement between the pin and the channel preferably prevents compression of the pin against the channel walls and thereby minimizes the possibility of tooth fracture. A chamfered stop adjacent to the threaded portion of the pin seats against a correspondingly shaped open end of the channel to provide a positive stop for the pin, which is dimensioned to stop before reaching the bottom of the channel, as well as a seal for the open end of the channel. A supra-coronal portion of the pin is dimensioned to extend a predetermined distance above the dentine surface and to provide the desired adhesion characteristics between the tooth and a coronal restoration. These first and second portions comprise the anchor portion of the pin structure. Finally, a manipulating portion of the pin provides a flat engagement surface for drivingly engaging with an operating tool together with a coupling-engagement means for fixing the manipulating portion in a socket of the tool. The manipulating portion is intended to transmit torque through a torque-limiting device, such as a frangible link, to the anchor portion of the pin. As the stop of the pin seats against the open end of the pre-drilled hole, the force required to rotate the pin exceeds the shear strength of the frangible link which, after forming the above-mentioned seal, fractures to automatically release the anchor portion from the manipulating portion.

BRIEF DESCRIPTION OF THE DRAWINGS

FIG. 1 is a side view of a dentinal pin structure incorporating a manipulating section according to the invention;

FIG. 2 illustrates a dentinal pin according to the invention installed in the dentinal portion of a damaged tooth;

FIG. 3 illustrates the cooperative coupling of a manipulative section with a socket driver, according to the invention;

FIG. 4 is a partial longitudinal sectional view of a pin as shown in FIG. 1 installed in a socket driver as shown in FIG. 3;

FIG. 5 is a transverse section taken on line 5—5 of FIG. 4;

FIG. 6 is a transverse section taken on line 6—6 of FIG. 4;

DETAILED DESCRIPTION OF THE DRAWINGS

Figure 7:
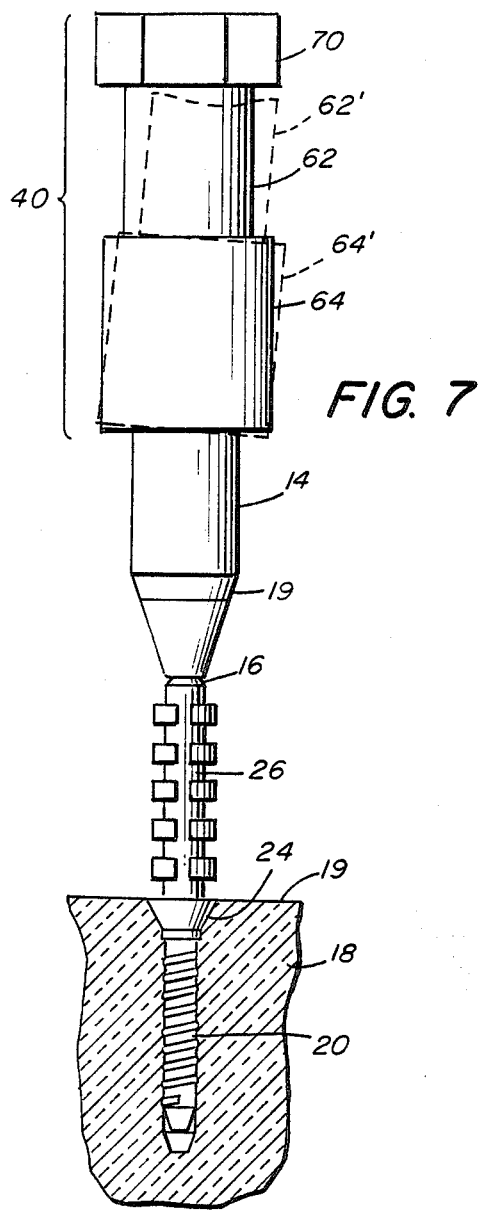
FIG. 7 is a side view of a dentinal pin being screwed into hole pre-formed in dentin, with a hand-type socket driver.

The pin structure 10 shown in FIG. 1 incorporates a dentinal pin 12 and a manipulator 14 connected together endwise by a torque-limiting device in the form of a frangible joint 16. The dentinal pin 12 has a threaded section 22 which is intended to be screwed into a hole 20 drilled in the dentinal portion 18 of a damaged tooth, as is shown in FIG. 2. The threaded section 22 is shorter than the depth of the hole 20, and a stop section 24 of the pin is, for example, conically shaped to fit in a similarly-shaped bevel 24' at the opening to the hole, for stopping the threaded section short of the bottom of the hole, and sealing the entrance to the hole. When the threaded section 22 is screwed into the hole, the stop section seats itself in the beveled opening 24', resisting further turning of the screw section, which also seals the opening by pulling the stop tightly onto the bevel 24'. Further forcing of the manipulator 14 puts torque on the frangible joint 16, which is dimensioned to break under the force of the torque if turning force is maintained against the resistance offered by the stop section 24. Thereafter, the pin 12 is left in the dentine 18, as is shown in FIG. 2, with its supracoronal section 26 sticking out above the surface 19 of the portion of dentine that is shown.

It will be recognized that the surface 19 is the bottom of a cavity or the like in a damaged tooth (not shown), wherein a restoration, filling, or the like is to be made, and the supracoronal section 26 is provided to support and to retain such a restoration. To that end, the sides of the supracoronal section 26 are preferably roughened or otherwise fitted with means to hold or bond to dental restoration materials.

The manipulator 14 is preferably round in cross section, tapering along a sidewall portion 37 at its remote end 34 to a smaller diameter toward its extremity 30. A sectoral portion 32 of the remote end is removed, leaving a flat sectoral wall 36 extending from the extremity 32 inward in the axial direction at the remote end, for engagement with a tool driver (to be described with reference to FIG. 3, etc.). A circumferential groove 38 is provided near the remote end, for engagement with a tool holder (also described with reference to FIG. 3, etc.). In use, the manipulator 14 is engaged in a tool-holder, and rotated around its longitudinal axis by a tool driver (both of which are desirably incorporated in the same structural entity) for threading the pin 12 into the hole 20. According to the invention, the tool holder and driver permits the pin to orient its longitudinal axis so as to align itself with the hole, as will presently be disclosed.

FIG. 3 illustrates the novel combination of features of a unitary tool holder and driver 40 according to the invention, and its cooperation with a pin structure as shown in FIG. 1. The tool holder and driver is a rigid tubular body 42 providing a cylindrical socket 44 the diameter of which is larger than the diameter of the manipulator 14. An "O" ring 48, made of a resilient material such as rubber, is fixed in the socket 44 near the opening 43 to the socket which confronts the extremity 30 of the manipulator. The manipulator is engaged in the socket by pushing the manipulator into the socket until the "O" ring 48 is engaged in the circumferential groove 38. This requires only motion that is generally parallel to the cylindrical axis A—A of the socket 44 and to the longitudinal axis of rotation B—B of the pin structure 10.

Farther in the socket 44, a sectoral block 55 provides a flat sectoral wall 56 which extends a distance generally parallel to the socket axis A—A that is approximately the same as the axial dimension of the sectoral wall 36 of the manipulator 14. When the manipulator 14 is engaged in the holder means, consisting in this illustration of the "O" ring 48 and groove 38, the tapered portion of the remote end 34 between the sectoral wall 36 and the inwardly-tapering side wall 37 will penetrate into a driver section 58 of the socket 44, where the sectoral wall 56 in the socket and the sectoral wall 36 of the manipulator will confront each other, without necessarily touching each other. Rotation of the tool holder and driver 40 around its tubular axis A—A will bring these two walls together along a contact line, forcing the pin structure 10 to rotate around its longitudinal axis B—B. However, as will presently be described with reference to FIGS. 4, 5 and 6, the axis B—B of the pin structure and the axis A—A of the tool holder and driver are not constrained to be parallel to each other; rather, according to the invention, within certain limits, the angular relation between these two axes is free to vary, permitting the pin structure to move relative to the tool holder and driver, and to find its own axis with relation to the hole 20 in the tooth.

The tool holder and driver 40 is made of two parts, a rigid tubular socket member 64 and a drive-shaft member 62, which are fastened together in any convenient way, to form a unitary tool holder and driver. The "O" ring 48 is fixed in the tubular socket member 64. The sectoral block 55 providing the sectoral driver wall 56 is fixed in the drive-shaft member 62, wherein the driver section 58 of socket 44 is defined. In the detailed embodiment shown in FIG. 3, a tubular driving gear member 57 receives the shaft member 62 and in turn is received in the socket member 64, these three parts being fixed together to form the tool holder and driver 40.

In FIG. 4 a manipulator 14 is shown mated with the tool holder and driver 40 which in FIG. 4 is illustrated only schematically, to simplify the illustration. The inner diameter $D_1$ of the tubular socket member 64 is larger than the outer diameter $D_0$ of the manipulator 14, which is resiliently supported and held in the socket 44 by the "O" ring 48. These relative dimensions are shown also in FIG. 6. The tapered wall 37 of the remote end 34 of the manipulator extends directly into the driver section 58 of the socket, without touching the socket walls, whereby the manipulator 14 is free to oscillate in the "O" ring 48, within certain limits that are reached when a wall (37, 36) of the remote end 34 touches a wall of the socket 44, 58. The tapered remote end 34 assures not only that the manipulator will be easily inserted into the socket, but also that these limits will be adequate to permit the tool (e.g: the pin 12) to move and find its own axis.

The end 61 of the drive shaft 62 that is within the upper end (in FIG. 3) of the tubular socket member 64 is also in the tubular driving gear member 57 with the sectoral block 55 fitted in it, as appears in FIG. 5. When the drive shaft is rotated around its axis, as is indicated, for example, by an arrow 68, the sectoral wall 56 of the drive shaft turns in the same rotational direction, as the dashed line 56' indicates, until it makes contact along a line with the sectoral wall 36 of the manipulator 14, forcing the manipulator to rotate in the same direction. The tubular socket member 64 rotates with the drive shaft member, carrying the manipulator in the "O" ring with it. Thus, the pin 12 is screwed into the dentinal hole 20 while being at all times free to seek its own axis with respect to the axis of the hole.

Referring again to FIG. 3, the tool driver and holder 40 is rotationally mounted in a support 59, for holding it in a dental handpiece and presenting its driving gear member 57 to a drive shaft (not shown) of conventional design.

A pin 12 is shown in FIG. 7 being screwed into the dentinal hole 20 with a tool holder and driver 40 fitted with a hand nut 70 at its top, for hand operation. As is indicated in dashed lines at 64', the tubular axis of the tool holder/driver 40 can change to a different direction relative to the tool axis while the tool maintains an axial direction that is suitable for screwing the pin 12 into the dentinal hole.

Figure 8:
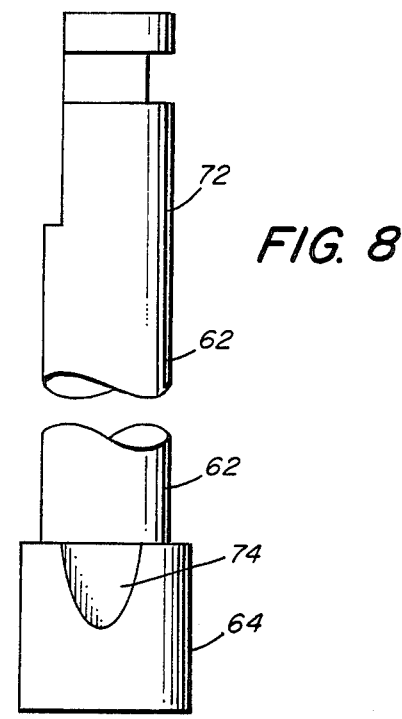
FIG. 8 is a side view of a motor-driven socket driver of the invention fitted with an adaptor for installation in a conventional dental contra-angle handpiece.
Figure 9:
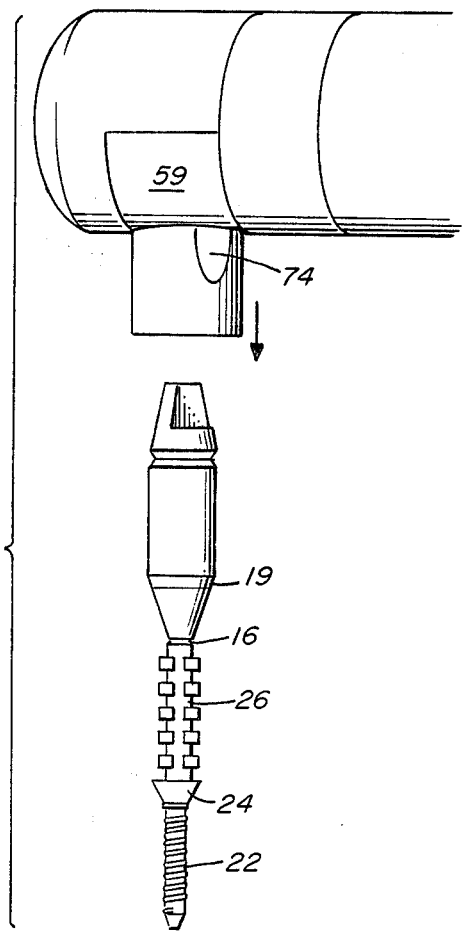
FIG. 9 shows in a general way the fitting of a miniaturized dental tool into a motor-driven socket driver, according to the invention.

The tool holder and driver can be fitted for motor drive in any of the conventional hand-pieces, contra-angles and the like that are available to dentists. FIG. 8 shows one example, in which the drive shaft 62 has a coupling head 72 of a well-known form that is in common use. Also shown in FIG. 8 is an indicator mark 74 on a side wall of the tubular socket member, for locating the sectoral driver wall 56 with respect to the manipulator sectoral wall 36 when inserting a pin structure 10 into the socket 44, as is illustrated in FIG. 9, which shows in outline form a miniaturized contra-angle designed to receive the support 59 that is shown in FIG. 3.

Figure 10:
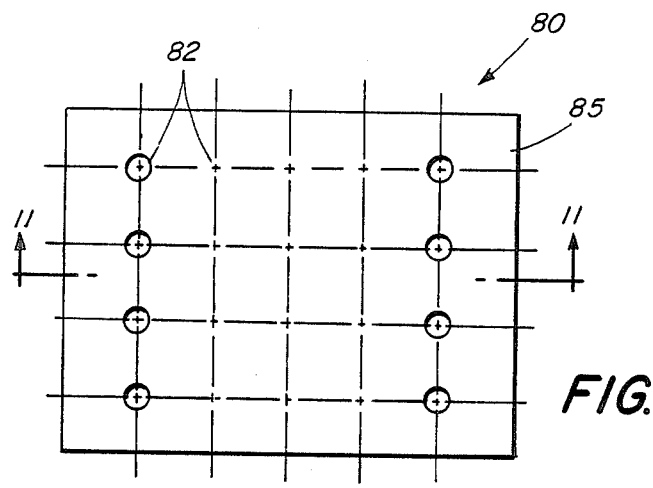
FIG. 10 is a plan view of a storage and delivery tray for a quantity of dentinal pin structures.

In order to accommodate various sizes of teeth, pin structures 10 are provided in various sizes, for example, four different sizes of the dentinal pins 12, and the sizes are made distinguishable, one from the others, by color-codes on a circumferential band 19 around the manipulator 14. The manipulators for all the pins are of one size, having an outer diameter $D_0$ about 1.6 mm. A storage and delivery tray 80 for a quantity of pin structures of one size is shown in FIG. 10. In practice, a supply of pin structures will be delivered to the dentist in a box (not shown) containing, e.g: four trays 80, one for each size, together with appropriate drills for forming holes 20 of suitable size and shape for each size pin structure, and one or more tool holder and driver components 40 with suitable driving mechanisms. FIGS. 10-14 illustrate the storage and delivery capabilities of the invention.

Figure 11:
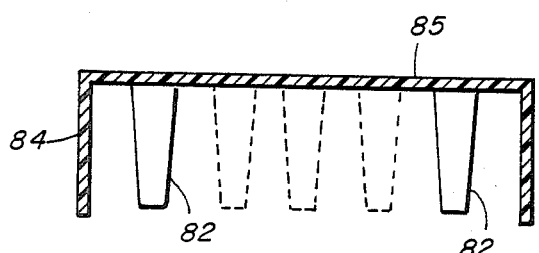
FIG. 11 is a section on line 11—11 of FIG. 10.

With reference to FIG. 10, the tray 80 is provided with a quantity of storage channels 82, one for each pin structure. The tray 80 may be constructed of a solid block (not shown) in which the channels 82 are formed, or of a single molded sheet 84, for example, of a plastics material, as shown in FIG. 11. The channels 82 are dimensioned to receive and hold the dentinal-pin portion 12 of a pin structure 10.

Figure 12:
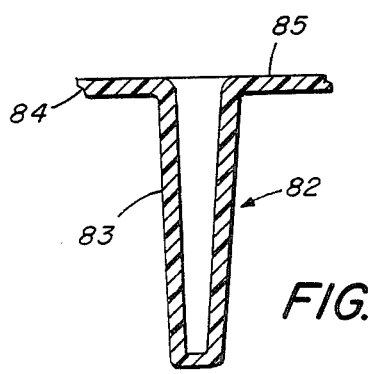
FIG. 12 is an enlarged view of a pin storing channel of the tray.

FIG. 12 is an enlarged sectional view of one of the channels 82. The channel wall 83 is preferably made of a resilient material which will frictionally retain the pin 12 but not cause any damage to the pin, and will easily release it. One pin 12 is inserted into each of the channels 82, so that the manipulator 14 engages the top surface 85 of the tray, with its color band 19 visible. Channels 82 serve to enclose the threaded portion 22 of each pin 12, to protect the threaded portion 22 from becoming damaged, and to minimize the possibility that any grit or infection-causing material may become imbedded in the threads.

Figure 13:
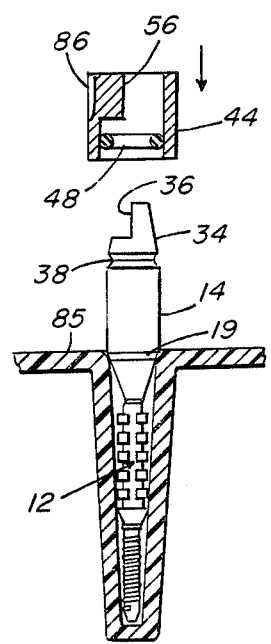
FIG. 13 shows a pin structure being picked up from the tray with a socket driver.

In addition, due to the extremely small size of the pins, the effective manual insertion of a pin 12 into the tool holder and driver 40 is difficult. Accordingly, as is shown in FIGS. 9 and 13, the socket 44 may conveniently engage one of the pin structures by pressing the socket down over the tapered portion of the remote end 34 of the manipulator 14 so that the O-ring 48 engages the circumferential groove 38. The driving face 36 of the manipulator and the corresponding driving face 56 of the tool holder and driver 40 may be aligned by rotating the socket 44 until a light reflective mark 86 on the outer surface of the socket is seen to reflect light in line with light reflected from the flat surface 36 of the manipulator portion 14 of the pin. The socket 44 may then pass down over the remote end 34 of the manipulator 14 so that the drive surfaces 56 and 36 are aligned when the O-ring 48 engages in the groove 38.

What is claimed is:

1. A tool operator for removably holding an elongated dental tool at a manipulative end thereof and rotating said tool around its longitudinal axis, comprising a rigid tubular socket open at its first end for receiving said manipulative end of said tool into said socket through said first end thereof,
    resilient annular tool-retaining means in said socket near said first end thereof adapted to engage the sides of said tool near said manipulative end thereof for resiliently and removably holding said tool in said socket, and
    tool driving means operative through the second end of said socket for engaging said manipulative end of said tool so as to rotate said tool around said longitudinal axis,
    in combination with an elongated dental tool removably received in said socket and intended in use to be rotated around its longitudinal axis,
    the external diameter of said manipulative end of said tool being smaller than the internal diameter of said tubular socket,
    said tool having on its side wall annular groove means removably received by said resilient tool-retaining means by pushing said tool into said socket in its axial direction,
    said tool having means axially extending from said manipulative end thereof remote from said groove means and operative upon entrance of said tool into said socket to engage said tool driving means.

2. For use in combination with a tool operator according to claim 1, said tool having on its side walls near said one end thereof means to cooperate with said resilient tool-retaining means, said tool having axially extending from said one end thereof means operative during entrance of said tool into said socket to engage said tool driving means.

3. The combination of a tool operator according to claim 1 wherein the internal diameter of said socket is larger than the external diameter of said one end of said tool, and said resilient tool-retaining means is an O-ring fitted in said socket near said first end thereof, for permitting the longitudinal axis of said tool to rock within said "O" ring and thereby change direction relative to the tubular axis of said socket while being removably retained in said socket by said O-ring.

4. In a combination according to claim 1, means including said driving means to mount said socket at the second end thereof for rotation around the tubular axis of said socket, and means to rotate said driving means together with said socket around said tubular axis.

5. In the combination according to claim 1, having extending axially from one end thereof said manipulative end, and a dentinal retention pin having in axial succession a threaded portion for engagement in a hole in dentinal material and a supra-coronal portion for supporting a dental restoration, said manipulative end being connected to and extending from said supra-coronal portion.

6. The combination according to claim 5 wherein said pin includes a penetration stop member fixed between said threaded portion and said supra-coronal portion, for stopping penetration of said threaded portion short of the bottom of a hole formed in said dentinal material with depth greater than the length of said threaded portion, and wherein said manipulative section is joined to said one end of said tool via a torque-limiting connector.

7. In a combination according to claim 1 wherein said resilient annular tool-retaining means includes a resilient member retained in said socket permitting the longitudinal axis of said tool to rock and to change angular direction relative to the tubular axis of said socket.

8. In a combination according to claim 1 wherein said resilient annular tool-retaining means is disposed in said socket close to its first end while said tool driving means is disposed in said socket more remote from said first end whereby the engagement between said resilient annular tool-retaining means and said annular groove forms a fulcrum permitting the longitudinal axis of said tool to rock and to change angular direction relative to the tubular axis of said socket.

9. In the combination according to claim 1, said dental tool comprising a generally round elongated dentinal retention pin having a first threaded section for threadedly engaging in a pre-drilled hole in the dentine of a tooth the coronal part of which has been at least partly removed, said hole having a depth greater than the length of said first section, a second penetration stop section fixed to said first section for limiting penetration of said first section short of the bottom of said hole, a third supra-coronal section fixed to and extending endwise from said second section on which to support a restoration of said removed coronal part of said tooth, and a fourth manipulatory section comprising said manipulative end attached endwise to said third section for screwing said first section into said hole, said manipulating section tapering to a reduced transverse sectional dimension at its extremity, said manipulative section having a sectoral portion removed in a limited region extending from near said extremity to said extremity so as to provide a substantially flat-wall segment extending to said extremity for imparting to said manipulative sectional force to turn said pin on its longitudinal axis.

10. In the combination according to claim 9, said holder for gripping and turning said dentinal retention pin comprising a rigid tubular socket having a tubular passage of larger internal diameter than the external diameter of said manipulative section, for receiving said manipulative section into said passage through a first end thereof, resilient means extending into said passage near said first end for gripping the side walls of said manipulative section, said manipulative section having a circumferential groove located between said extremity and said third section for engaging said resilient gripping means, driving means further in said socket for engaging said flat wall section by end-wise approach when said extremity reaches into said socket after insertion of said manipulative section through said first end, and means to rotate said holder for rotating said pin around its longitudinal axis, said pin axis being free within a limited range to rock about said resilient means thereby to change direction relative to the axis of rotation of said holder.

11. In the combination according to claim 10 a holder wherein said driving means includes an inner socket section for endwise receiving said tapered extremity of said manipulative section, and a sectoral block having a substantially flat face for engaging said flat wall segment of said manipulative section, said inner socket section being dimensioned to permit said tapered extremity to move transversely a limited distance therein so as to allow said pin axis to change its direction relative to said axis of rotation by pivotal motion around said resilient gripping means as a fulchrum.

12. In the combination according to claim 11 an index mark on the exterior of said rigid tubular socket for aligning said flat face of said sectoral block with the flat wall segment of said manipulating section, prior to inserting said manipulating section into said socket passage through said first end thereof.

13. A tool operator according to claim 1 wherein the dental tool manipulative end and the tubular socket end for receiving said manipulative end are relatively dimensioned to permit said manipulative end to move transversely a limited distance therein so as to allow the axis of the tool to change direction relative to the axis of rotation of the tool driving means to enable self-alignment therebetween.

14. A tool operator according to claim 13 wherein the axis of the tool changes its direction relative to the axis of rotation of the tool driving means by pivotal motion around said resilient tool-retaining means.

* * * * *